(12) United States Patent
Mahmoudabadi et al.

(10) Patent No.: US 12,710,523 B2
(45) Date of Patent: Aug. 18, 2026

(54) METHODS AND SYSTEMS FOR TESTING ACOUSTIC TRANSDUCERS, AND ACOUSTIC TRANSDUCER ADAPTERS FOR THE SYSTEMS

(71) Applicant: LENARD ENTERPRISES INC., Newmarket (CA)

(72) Inventors: Hodjatallah Mahmoudabadi, Newmarket (CA); Hamidreza Moshayedi, Arak (IR)

(73) Assignee: LENARD ENTERPRISES INC., Newmarket (CA)

( * ) Notice: Subject to any disclaimer, the term of this patent is extended or adjusted under 35 U.S.C. 154(b) by 369 days.

(21) Appl. No.: 18/392,519

(22) Filed: Dec. 21, 2023

(65) Prior Publication Data

US 2024/0210544 A1 Jun. 27, 2024

Related U.S. Application Data

(60) Provisional application No. 63/476,554, filed on Dec. 21, 2022.

(51) Int. Cl.
*G01S 7/52* (2006.01)
*A61B 8/00* (2006.01)
(Continued)

(52) U.S. Cl.
CPC .............. *G01S 7/5205* (2013.01); *A61B 8/58* (2013.01); *A61B 8/587* (2013.01);
(Continued)

(58) Field of Classification Search
CPC ..... G01S 7/5205; G01S 7/52082; A61B 8/58; A61B 8/587; G01M 99/008; G01N 29/30;
(Continued)

(56) References Cited

U.S. PATENT DOCUMENTS 5,763,773 A 6/1998 Birchak et al.
7,028,529 B2 4/2006 Gessert et al.
(Continued)

FOREIGN PATENT DOCUMENTS

WO 2022136077 A1 6/2022

OTHER PUBLICATIONS

Sonora Medical Systems, Inc., "Safe Probes. Safe Patients. Safe Budgets. FirstCall aPerio".
(Continued)

*Primary Examiner* — Ryan D Walsh

(57) ABSTRACT

An acoustic transducer adapter for coupling an acoustic transducer to a testing device is described herein. The acoustic transducer adapter includes: a main module operable to receive a test signal from the testing device; and an adapter module electrically coupled to the main module. The transducer module includes an adapter controller programmable to be compatible with different acoustic transducers; and a signal processing component for receiving one or more reflected signals from one or more respective transducing elements of the acoustic transducer in response to the test signal and converting the one or more reflected signals to a transducer data signal representative of an operation state of the acoustic transducer. The adapter controller being operable to: receive the test signal from the main module; adapt the test signal based on one or more operating parameters of the acoustic transducer; and transmit the test signal to the acoustic transducer.

23 Claims, 13 Drawing Sheets

(51) Int. Cl.
*G01M 99/00* (2011.01)
*G01N 29/30* (2006.01)
*G01N 29/44* (2006.01)

(52) U.S. Cl.
CPC .......... *G01M 99/008* (2013.01); *G01N 29/30* (2013.01); *G01N 29/4436* (2013.01); *G01S 7/52082* (2013.01); *B06B 2201/40* (2013.01); *G01N 2291/106* (2013.01)

(58) Field of Classification Search
CPC .......... G01N 29/4436; G01N 2291/106; B06B 2201/40
See application file for complete search history.

(56) References Cited

U.S. PATENT DOCUMENTS

| | | | | |
|---|---|---|---|---|
| 7,246,264 | B2 | 7/2007 | Grellmann et al. | |
| 7,278,289 | B2 | 10/2007 | Gessert et al. | |
| 8,792,295 | B2 | 7/2014 | Kristoffersen et al. | |
| 9,525,257 | B1 | 12/2016 | Moore et al. | |
| 9,594,062 | B2 | 3/2017 | Ginther | |
| 10,509,014 | B2 | 12/2019 | Segall | |
| 11,730,455 | B2 * | 8/2023 | Cao | A61B 8/145 600/447 |
| 2009/0240453 | A1 | 9/2009 | Straub, Jr. | |
| 2009/0260443 | A1 * | 10/2009 | Suita | G01N 29/0672 73/632 |
| 2011/0030448 | A1 | 2/2011 | Moore et al. | |
| 2014/0241115 | A1 * | 8/2014 | Thattari Kandiyil | G01S 7/52004 367/13 |
| 2016/0131746 | A1 * | 5/2016 | Beaty | G01S 15/8915 367/13 |
| 2017/0089868 | A1 | 3/2017 | Beaty | |
| 2020/0000435 | A1 | 1/2020 | Anand | |
| 2024/0210543 | A1 * | 6/2024 | Mahmoudabadi | G01S 7/52079 |

OTHER PUBLICATIONS

Sonora Medical Systems, Inc., "FirstCall 2000 Ultrasound Probe Testing System—Users Guide".
Cannon, "DL Series ZIF connectors".

* cited by examiner 500
226c
120
224
222
802
226b 500
226a
120
226d 900
102
103
105
110
114
350
354
204
352
310
312
314
316
318
320
322
112
226
120
224
202a
214
212
222
202b
204
POWER
REFLECTED SIGNAL
REFLECTED SIGNAL DATA
FOR POWER SETTING
TO PROBE ASIC
TO DRIVE THE ANALOG SWITCHES

METHODS AND SYSTEMS FOR TESTING ACOUSTIC TRANSDUCERS, AND ACOUSTIC TRANSDUCER ADAPTERS FOR THE SYSTEMS

CROSS-REFERENCE TO RELATED APPLICATIONS

This application claims benefit of U.S. Provisional Patent Application No. 63/476,554 filed on Dec. 21, 2022. The entire content of U.S. Provisional Patent Application No. 63/476,554 is hereby incorporated by reference in its entirety.

FIELD

The described embodiments relate to methods and systems for testing acoustic transducers, and acoustic transducer adapters for the systems. More specifically, the described embodiments relate to ultrasound transducers.

BACKGROUND

Acoustic transducers can operate to convert sound wave vibrations to mechanical and/or electrical energy. One example of an acoustic transducer is an ultrasound transducer. Ultrasound is an imaging technique that uses sound wave vibrations to produce images of structures, such as organs within a human body. The images can provide information for diagnostic purposes and for directing treatment for a variety of diseases and conditions.

A typical ultrasound transducer includes a transducer head with transducing elements, which are usually formed of piezo-electric material. The number of transducing elements can vary but are typically in the range of 64 to 256. Fewer or greater number of transducing elements can be included at the transducer head. Different transducer heads may be applied for different purposes. A different size and/or shape of the transducer head can be more appropriate for producing images of specific structures. Example types of ultrasound transducer heads can include, but are not limited to, convex, linear, intraoperative linear, hockey stick linear, intrarectal micro convex, intraoperative linear, endo-cavity micro-convex, and phased array. For example, a micro-sized ultrasound head is more suitable for conducting an endoscopic examination of small cavities, such as mouth.

As best operation practice, ultrasound transducers should be regularly maintained and tested to identify any malfunction. Traditional methods of testing ultrasound transducers can be cumbersome as trained technicians may be required to properly test the transducer and/or diagnose any resulting test results. Further, testing equipment may not always be available, or properly calibrated or set up (e.g., with the proper transducer adapters and cables for the type and/or model of the various transducer) at the institution in which the ultrasound transducers are being used. Ultrasound transducers are often used in large and busy institutions such as hospitals and/or medical clinics, and so, the upkeep of frequently used diagnostic equipment can be overlooked.

It is possible for the institutions to have the transducers off-site for evaluation, but that would lead to significant down-time for the transducers. The off-site testing location will still require all the various connectors and test equipment specific to the type and/or model of the transducers.

SUMMARY

The various embodiments described herein generally relate to methods (and associated systems configured to implement the methods) for testing acoustic transducers, and acoustic transducer adapters for the systems disclosed herein.

In accordance with an example embodiment, there is provided an acoustic transducer adapter for coupling an acoustic transducer to a testing device. The acoustic transducer adapter includes a main module in communication with the testing device, the main module operable to receive a test signal from the testing device; and an adapter module electrically coupled to the main module, the adapter transducer module including: an adapter controller programmable to be compatible with a plurality of different acoustic transducers, the adapter controller operable to: receive the test signal from the main module; adapt the test signal based on one or more operating parameters of the acoustic transducer; and transmit the test signal to the acoustic transducer; and a signal processing component for receiving one or more reflected signals from one or more respective transducing elements of the acoustic transducer in response to the test signal and converting the one or more reflected signals to a transducer data signal representative of an operation state of the acoustic transducer.

In some embodiments, the main module and the adapter module are stacked.

In some embodiments, the main module is provided on a first printed circuit board and the adapter module is provided on a second printed circuit board electrically coupled to the first printed circuit board.

In some embodiments, the signal processing component includes one or more analog switches.

In some embodiments, the signal processing component includes a multiplexer.

In some embodiments, the adapter module includes an adapter module connection port for coupling the adapter module to the acoustic transducer, and a protective circuit intermediate the adapter controller and the adapter module connection port.

In some embodiments, the signal processing component is operable to receive an operational signal from the main module.

In some embodiments, the adapter controller is programed to be compatible for communication with the acoustic transducer prior to initiating testing of the acoustic transducer.

In some embodiments, the plurality of different acoustic transducers includes one or more acoustic transducers manufactured by different manufacturers.

In some embodiments, the acoustic transducer includes an ultrasound transducer.

In some embodiments, the main module includes: a main controller for receiving the test signal from the testing device; and a pulser circuit for generating an impact signal based on the test signal and transmitting the impact signal to the adapter module, resulting in an impact response signal being generated from the acoustic transducer in response to the high voltage signal.

In some embodiments, the main module further includes a switch intermediate the pulser circuit and the adapter module, the switch operating to transmit the impact signal to the adapter module from the pulser circuit and to receive the impact response signal from the signal processing component.

In some embodiments, the main module further includes an amplifier for amplifying the impact response signal received from the signal processing component.

In some embodiments, the impact signal includes a high voltage signal.

in some embodiments, the main module further includes a first main module connection port for coupling the main module to the testing device to communicate via one or more analog switch or multiplexer, and a second main module connection port for coupling the main module to the acoustic transducer.

In some embodiments, the main module further includes a switch intermediate the pulser circuit and the signal processing component, the switch operating to transmit the impact signal to the acoustic transducer via the signal processing component and to receive the impact response signal from the acoustic transducer via the signal processing component.

In some embodiments, the main module further includes an amplifier to amplify the impact response signal received from the acoustic transducer via the signal processing component, and one or more filters to remove noise from the received impact response signal.

In accordance with an embodiment, there is provided an acoustic transducer testing system. The system includes a device controller operable to generate a test signal; and one or more connection ports for coupling to one or more acoustic transducer adapters for receiving the test signal to test one or more different acoustic transducers.

In accordance with an embodiment, there is provided a method of testing an acoustic transducer. The method includes transmitting an impact signal to one or more transducing elements of the acoustic transducer; receiving an impact response signal from the one or more transducing elements in response to the impact signal and a reflected signal generated from a reflector in response to the impact signal; and evaluating the impact response signal and the reflected signal to determine an operation state of the acoustic transducer.

In some embodiments, the impact signal includes a high voltage signal.

In some embodiments, evaluating the impact response signal and the reflected signal to determine the operation state of the acoustic transducer includes evaluating the operation state of each transducing element.

In some embodiments, evaluating the impact response signal and the reflected signal to determine the operation state of the acoustic transducer includes evaluating the operation state of a transducer cable.

In some embodiments, the method further includes predicting a failure likelihood of the acoustic transducer based on the impact response signal, the reflected signal, and the operation state of the acoustic transducer.

BRIEF DESCRIPTION OF THE DRAWINGS

Several embodiments will now be described in detail with reference to the drawings, in which.

DESCRIPTION OF EXAMPLE EMBODIMENTS

The various embodiments described herein generally relate to methods (and associated systems configured to implement the methods) for testing acoustic transducers, and to acoustic transducer adapters for the systems disclosed herein. More specifically, the described embodiments can relate to ultrasound transducers.

Transducers operate to convert sound wave vibrations to mechanical and/or electrical energy. Typically, acoustic transducers include transducing elements that can vibrate when an electric signal is applied. The transducing elements can be composed of piezoelectric ceramic elements, for example. In ultrasound transducers, the transducing elements can then produce ultrasound waves. The transducing elements can also operate to produce electrical signals when sound waves are detected. Typically, the number of transducing elements include 64 to 256, but this number can increase or decrease depending on the design and/or application of the acoustic transducer.

When an ultrasound transducer is used on a human body, the ultrasound waves pass through the skin and into the internal anatomy. As the waves encounter tissues with different characteristics and densities, they produce echoes (reflected waves) that are then detected by the transducing elements on the ultrasound transducer. The ultrasound transducer then converts the reflected waves into electrical signals. The ultrasound device receiving the electrical signals can then translate the electrical signals into an image representing anatomic features.

Acoustic transducers are typically tested at regular intervals to ensure that its components (e.g., cable and/or transducing elements) are operating properly or at least at an acceptable operation state for the intended usage. Various methods (and associated systems configured to implement the methods) for testing acoustic transducers, and acoustic transducer adapters for the systems disclosed herein will be described.

Figure 1:
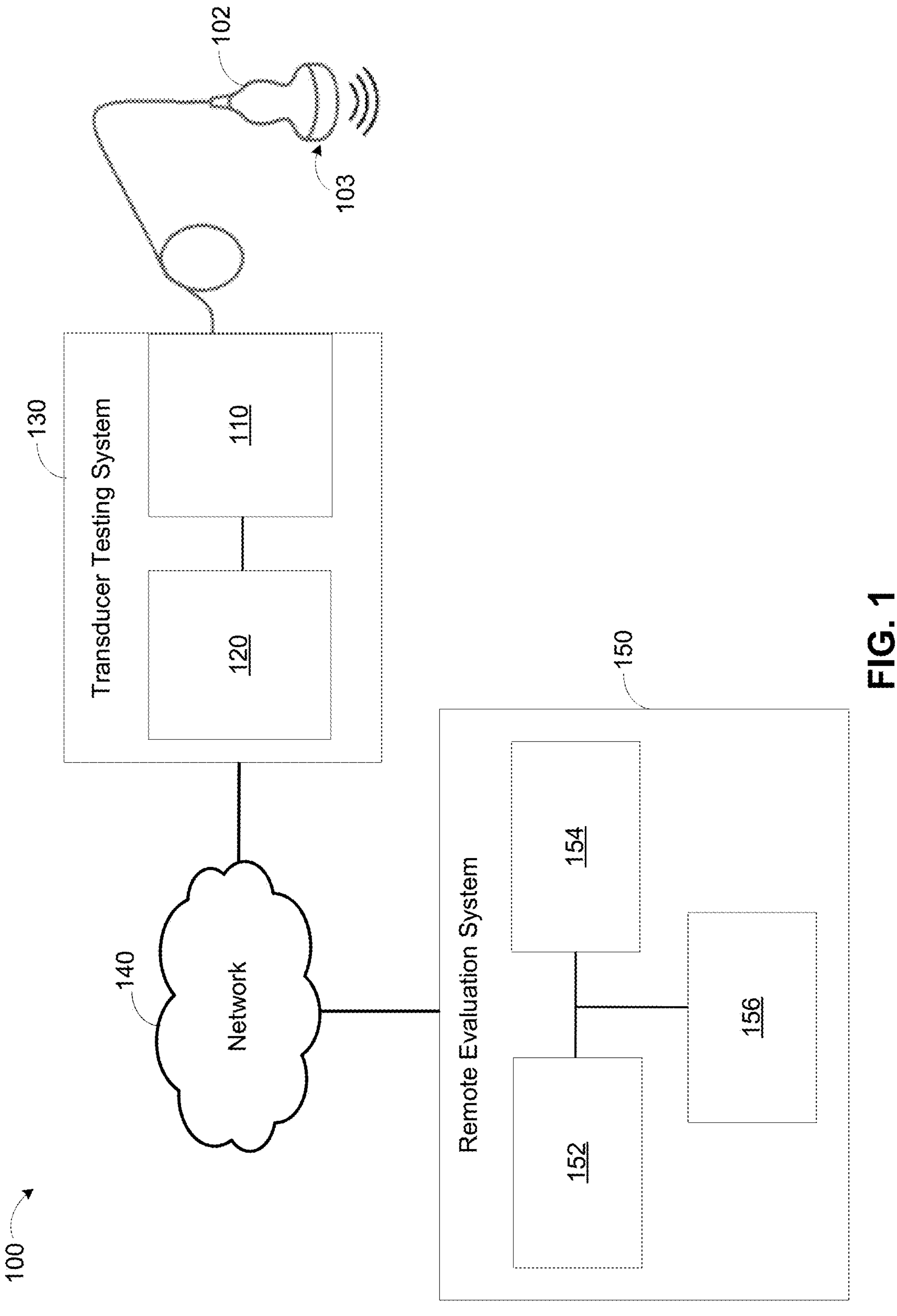
FIG. 1 is a block diagram of components interacting with a transducer testing system and a remote evaluation system in accordance with an example embodiment.

Reference is made to FIG. 1, which illustrates a block diagram 100 of components interacting with a transducer testing system 130 and a remote evaluation system 150 via a network 140.

The transducer testing system 130 operates to test the operation state of acoustic transducers, such as 102 shown in FIG. 1. When operation state data is collected by the transducer testing system 130, the transducer testing system 130 can transmit the operation state data in respect of the acoustic transducer 102 via the network 140 to the remote evaluation system 150 for determining the operation state of the acoustic transducer 102. In some embodiments, the transducer testing system 130 can determine the operation state of the acoustic transducer 102 locally without needing to transmit the operation state data to the remote evaluation system 150. The evaluation of the operation state of the acoustic transducer 102 may, in some cases, be more limited due to the more limited computational resources and/or data available at the transducer testing system 130.

Figure 2:
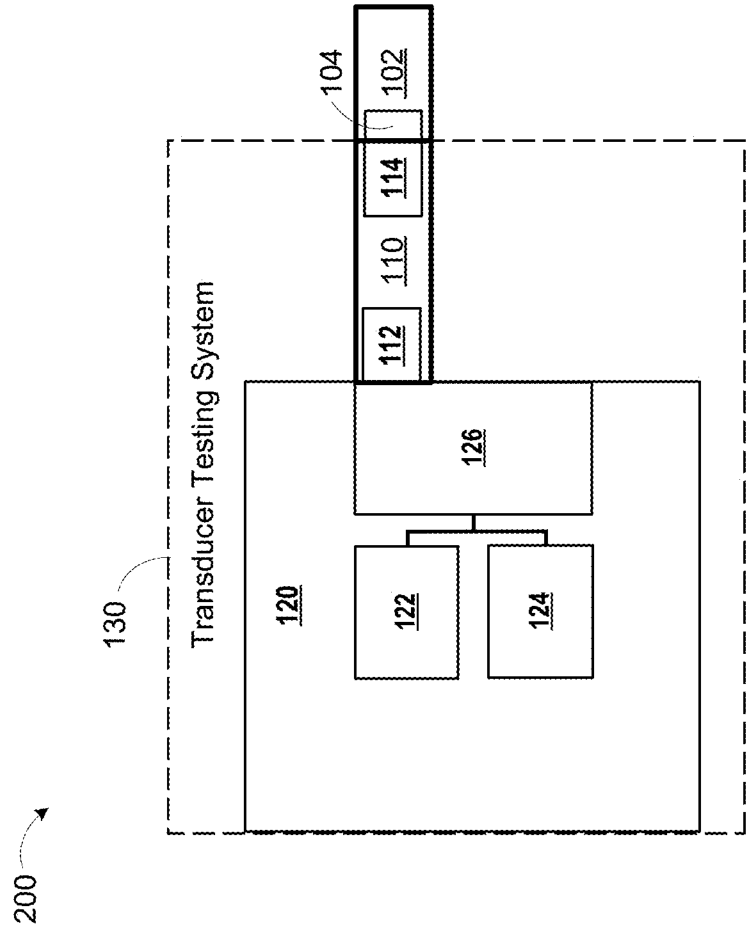
FIG. 2 is a block diagram of the transducer testing system in accordance with an example embodiment.

FIG. 2 shows an example block diagram 200 of the transducer testing system 130 in electrical communication with the acoustic transducer 102. The transducer testing system 130 can include one or more transducer adapters 110 for coupling a respective acoustic transducer 102 to a testing device 120. In FIGS. 1 and 2, only one acoustic transducer 102 is shown to be coupled to the testing device 120 via the transducer adapter 110 for ease of exposition. In some embodiments, the transducer testing system 130 can accommodate more than one acoustic transducer 102 to be coupled to the testing device 120 via respective transducer adapters 110.

The testing device 120 operates to transmit test signals to the acoustic transducer 102 via the transducer adapter 110 to initiate various tests of the acoustic transducer 102 to determine its operation state. As will be described, the test signals vary with the type of tests being conducted. The testing device 120 can also operate to receive a transducer data signal representative of the operation state of the acoustic transducer 102 via the transducer adapter 110.

The transducer adapter 110 and the acoustic transducer 102 can couple to each other via respective ports 114 and 104. Similarly, the transducer adapter 110 and the acoustic transducer 102 can couple to each other via respective ports 112 and 126.

Figures 3, 4:
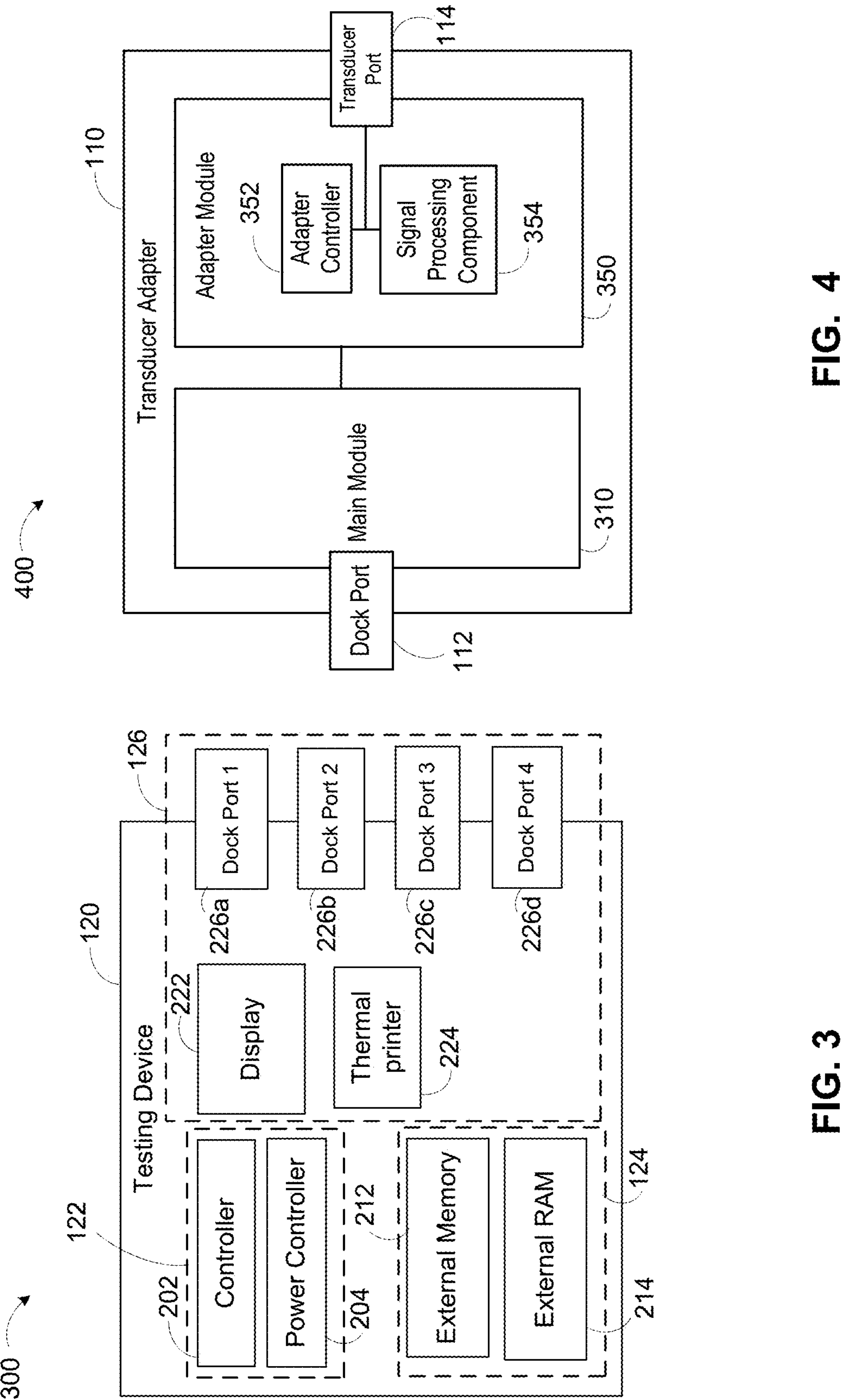
FIG. 3 is a block diagram of an example testing device in accordance with an example embodiment.
FIG. 4 is a block diagram of an example transducer adapter in accordance with an example embodiment.

The testing device 120 includes, at least, a device controller 122, a device storage component 124, and a device interface component 126. Reference will now be made to FIG. 3, which is a block diagram 300 of an example testing device 120.

The device controller 122 can operate to generate the test signals for testing the acoustic transducer 102 coupled via the transducer adapter 110. The device controller 122 may be any suitable processors, controllers or digital signal processors that can provide sufficient processing power depending on the configuration, purposes and requirements of the testing device 120. In some embodiments, the device controller 122 can include more than one processor with each processor being configured to perform different dedicated tasks. For example, the testing device 120 shown in FIG. 3 includes a device controller 202 and a power controller 204. Briefly, in the example shown in FIG. 9, the device controller 202 includes a first device controller 202*a* and a second device controller 202*b*.

Figure 8:
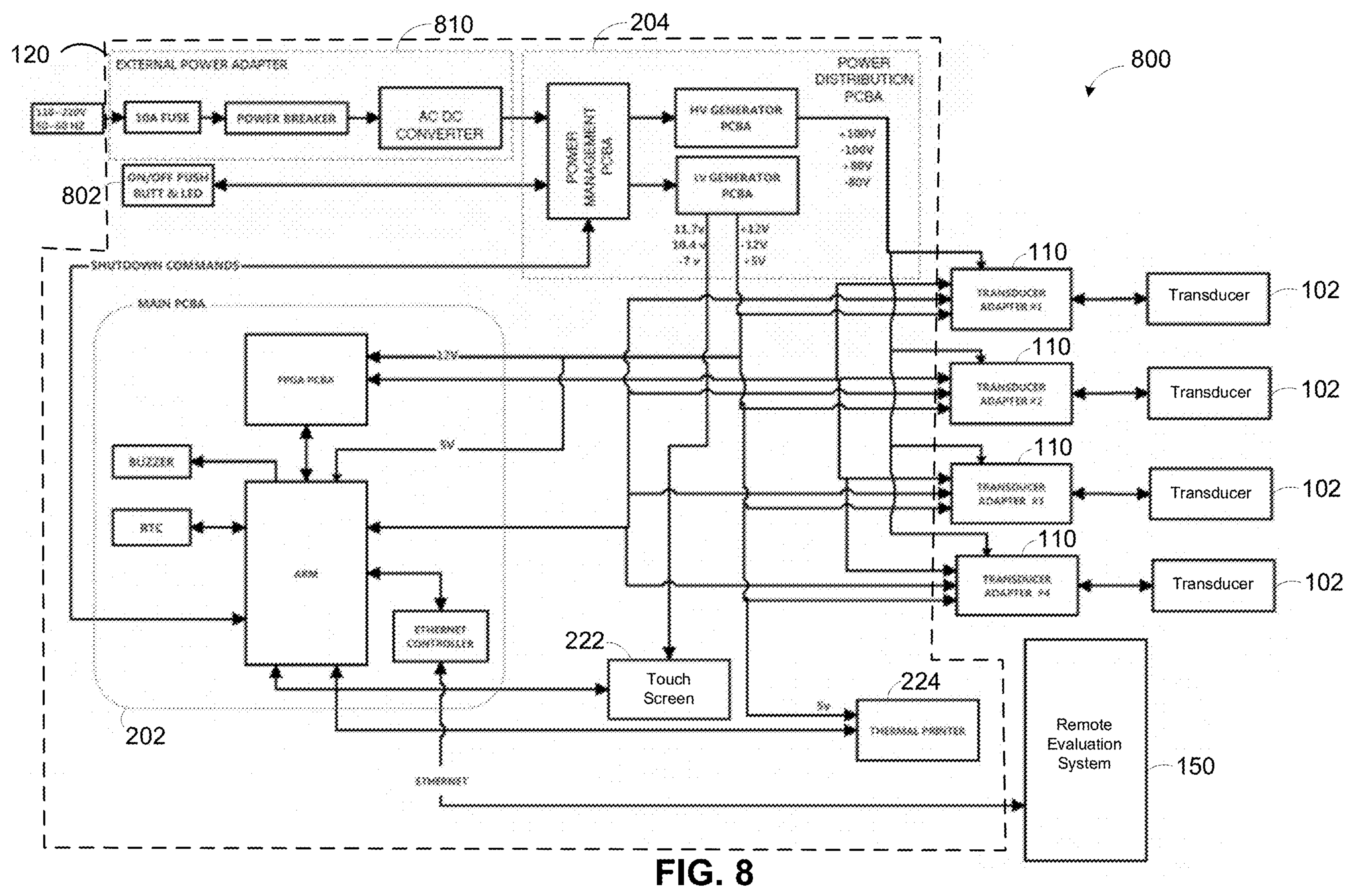
FIG. 8 is an example circuit diagram illustrating the testing system in communication with other components in accordance with an example embodiment.

The device controller 202 operates to generate the test signals for testing the acoustic transducer 102 coupled via the transducer adapter 110, and other operation of the testing device 120. The power controller 204 can operate to regulate the power usage of the testing device 120. Briefly, as shown in FIG. 8, the power controller 204 can manage the input stage of power as received via an external power adapter 810, and also for distribution of power to the various components of the testing device 120. The power controller 204 can also initiate and shut down operation of the testing device 120 on receipt of an on/off input received from a push button 802, as shown in the example circuit diagram 800 in FIG. 8. Other implementations of initiating and shutting down operation of the testing device 120 is possible.

The device storage component 124 can include RAM, ROM, one or more hard drives, one or more flash drives or some other suitable data storage elements, such as disk drives, etc. Referring again to FIG. 3, the testing device 120 can include an external memory 212 and an external RAM 214.

The device interface component 126 includes connection ports for coupling to one or more transducer adapters 110. The device interface component 126 can include any interface that enables the testing device 120 to communicate with other devices and systems. In some embodiments, the device interface component 126 can include at least one of a serial port, a parallel port or a USB port. The device interface component 126 may also include at least one of an Internet, Local Area Network (LAN), Ethernet, Firewire, modem or digital subscriber line connection for communicating with the remote evaluation system 150 and/or other transducer testing systems 130 via the network 140. Various combinations of these elements may be incorporated within the device interface component 126.

For example, in some embodiments, the device interface component 126 can receive input from various input devices, such as a mouse, a keyboard, a touch screen, a thumbwheel, a track-pad, a track-ball, a card-reader, voice recognition software and the like depending on the requirements and implementation of the testing device 120. In FIG. 3, for example, the device interface component 126 includes a display 222 for displaying test data generated based on the transducer data signal representative of the operation state of the acoustic transducer 102. The display 222 can also receive input from the operator of the testing device 120, which can be via a screen if touchscreen capability is available at the display 222, and/or via another input device.

Figure 5A:
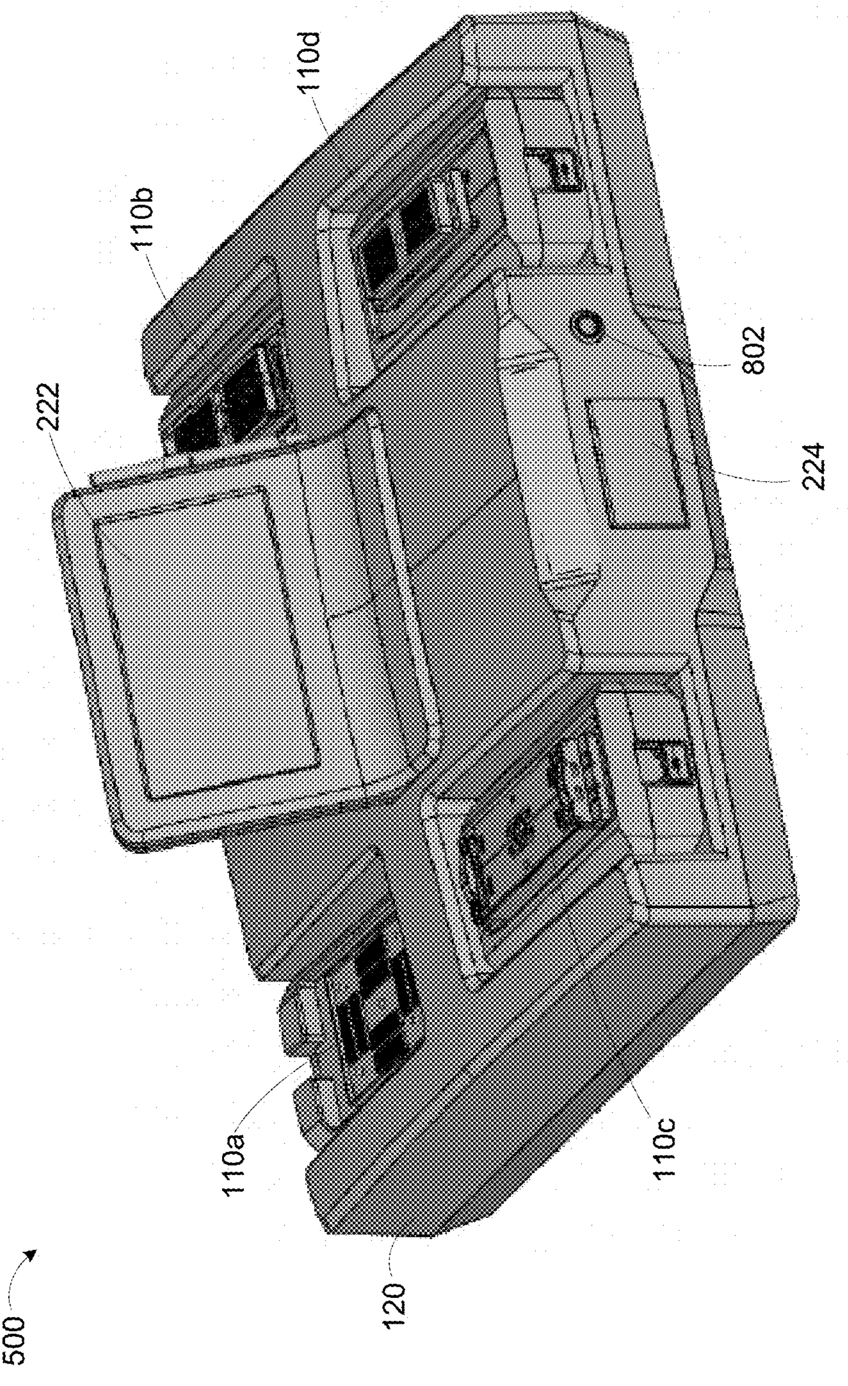
FIG. 5A is a perspective view of an example testing device coupled with example transducer adapters.
Figures 5B, 5C:
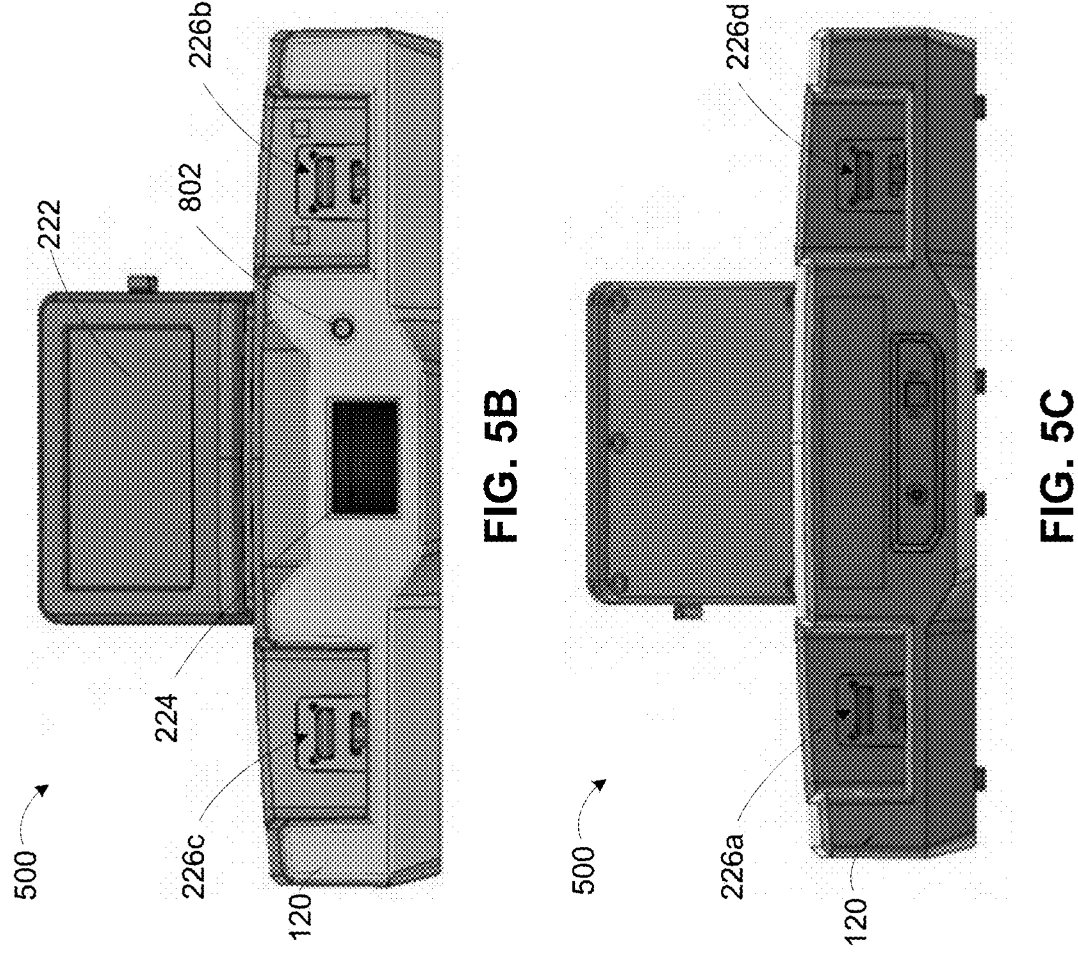
FIG. 5B is a front view of the example testing device of FIG. 5A.
FIG. 5C is a rear view of the example testing device of FIG. 5A.

The device interface component 126 can also include one or more dock ports 226, depending on the design and/or intended application of the testing device 120. In the example shown in FIG. 3, the device interface component 126 includes four dock connectors, 226*a* to 226*d*. Each dock connector 226 can couple to a respective port of a transducer adapter 110 (see e.g., dock connector 112 in FIG. 4). Other number of dock ports 226 can be included at the testing device 120, depending on the design and application of the testing device 120. An example testing device 120 coupled with transducer adapters 110*a* to 110*d* is shown generally at 500 in FIG. 5A. An example testing device 120 without coupled transducer adapters is shown generally at 500 in FIG. 5B and FIG. 5C. As shown in FIG. 5B and FIG. 5C, each of the dock ports 226*a* to 226*d* is configured to couple to a different type of dock port 112 of the respective transducer adapter 110*a* to 110*d* (see e.g., transducer adapters 110*a* to 110*d* in FIG. 5A). The dock port 112 of the transducer adapter 110 can vary with different manufacturers and/or versions of the transducer adapter even for the same manufacturer. So, it can be important for the testing device 120 to be able to accommodate a varied number of dock ports 112 depending on the type of institution in which the testing device 120 will be used. It will be understood that, in some embodiments, two or more of the dock ports 226*a* to 226*d* can be the same.

Other configurations of the testing device 120 is possible. For example, the testing device 120 can include no display 222 and/or only one dock port 226. The testing device 120 shown in FIGS. 5A to C is intended as only an example and not a limitation.

As the transducer adapter 110 can be removed from the testing device 120 and interchanged with another transducer adapter 110 designed for another type of acoustic transducer 102 if necessary, it can be more manageable for institutions to more regularly test acoustic transducers 102 as only one testing device 120 is likely required for the various different acoustic transducers 102 as long as the corresponding transducer adapter 110 is available.

The device interface component 126 can include a thermal printer 224, in some embodiments, for printing the test results and/or other data associated with the testing of the acoustic transducer 102. Other types of output device for generating a printout may be used. In some embodiments, the device interface component 126 can communicate the test results and/or data to the remote evaluation system 150 via the network 140 for display and/or further analysis.

It will be understood that in some embodiments, each of the device controller 122, the device storage component 124, and the device interface component 126 may be combined into fewer number of modules or may be separated into further modules.

Reference will now be made to FIG. 4, which is a block diagram 400 of an example transducer adapter 110.

Figures 6A, 6B:
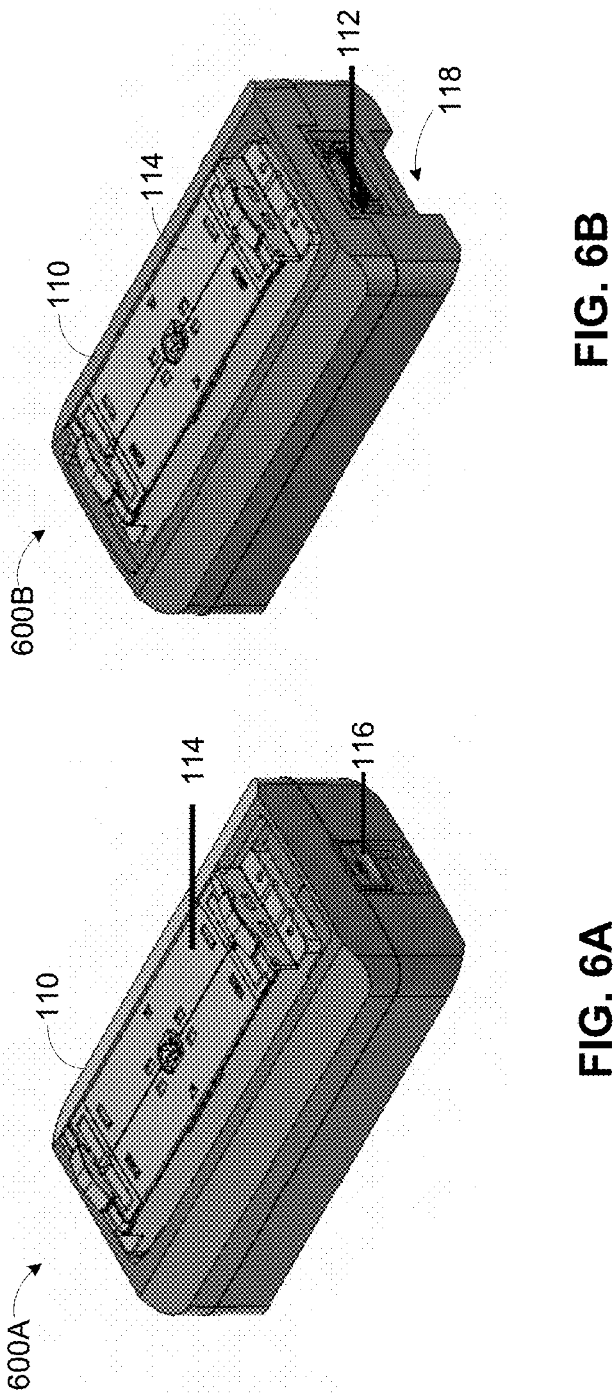
FIG. 6A is a front, perspective view of an example transducer adapter.
FIG. 6B is a rear, perspective view of the example transducer adapter of FIG. 6A.

The transducer adapter 110 includes a main module 310, and an adapter module 350 in electrical communication with the main module 310. The adapter module 350 includes an adapter controller 352 and a signal processing component 354. As shown in FIG. 4, the transducer adapter includes a dock port 112 for coupling to a dock port 226 at the testing device 120, and a transducer port 114 for coupling to the transducer adapter 110. FIGS. 6A and 6B show respective front and rear perspective views 600A and 600B of an example transducer adapter 110 configured for the testing device 120 shown in FIGS. 5A to C. The transducer port 114 will vary in structure depending on the type of acoustic transducer 102 for which the transducer adapter 110 is designed. Each transducer adapter 110 can typically accommodate a number of different acoustic transducer models.

The transducer adapter 110 can also include a locking mechanism 116 to lock the transducer adapter 110 to the testing device 120 when coupled. The transducer adapter 110 can include a guided rail (generally at 118), or a similar track-like mechanism to guide the transducer adapter 110 into a dock port 226 of the testing device 120.

When coupled to the testing device 120, the main module 310 is in communication with the testing device 120 via the dock port 112. The adapter module 350 is electrically coupled to the main module 310. The main module 310 is common for all transducer adapters 110 disclosed herein. To accommodate the various different designs of the acoustic transducer 102, such as the number of transducing elements and/or connection ports, the main module 310 includes the common components for enabling coupling between the testing device 120 and the acoustic transducer 102. As will be described, the adapter module 350 includes components programmable for adapting to the operating parameters of the acoustic transducer 102 to be tested.

Figure 9:
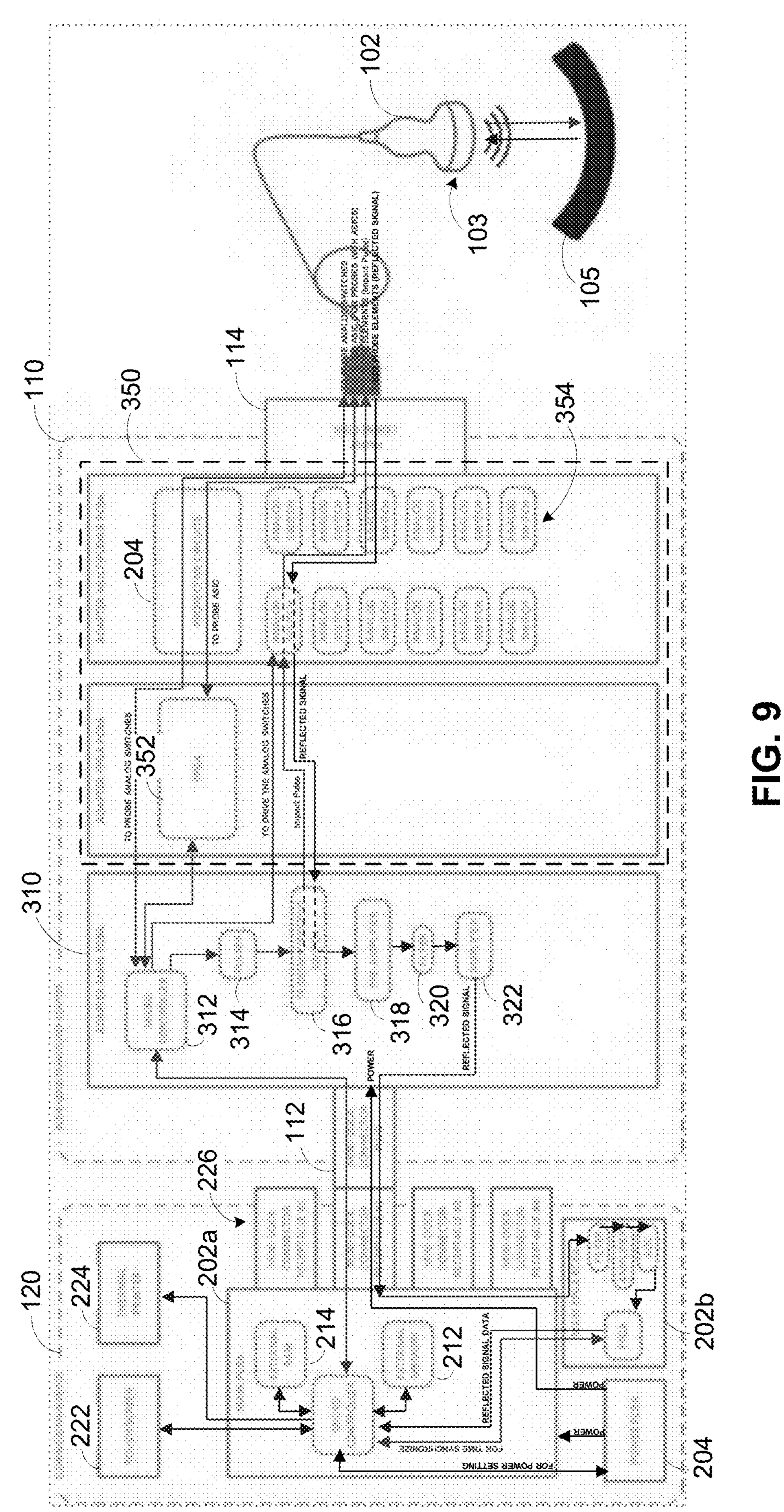
FIG. 9 is an example block diagram illustrating example data flows between the testing system, the transducer adapter and the acoustic transducer in accordance with an example embodiment.

Reference will now be made to FIG. 9, which is a block diagram 900 illustrating example data flows between the testing device 120, the transducer adapter 110 and the acoustic transducer 102 in accordance with an example embodiment.

As shown in FIG. 9, the main module 310 can operate to receive a test signal from the testing device 120 at a main controller 312. The main controller 312 can then transmit the test signal to the adapter module 350, which then adapts the test signal for the acoustic transducer 102 to be tested. When detected by the transducing elements 103 of the acoustic transducer 102, the transducing elements 103 convert the test signal from an electrical signal to a transducer signal (e.g., ultrasound signal when using an ultrasound transducer). The transducer signal is then transmitted from the head of the acoustic transducer 102 towards a reflector 105, when operating the acoustic transducer 102 for testing purposes. The transducing elements 103 of the acoustic transducer 102 detect a reflected transducer signal and converts it to a reflected electrical signal. The acoustic transducer 102 then transmits the reflected signal to the testing device 120 via the transducer adapter 110.

The main module 310 can include a pulser circuit 314 in some embodiments. For specific testing modes, such as an impulse response test as will be described with reference to FIGS. 10 to 12, the pulser circuit 314 can operate to generate an impact signal based on the test signal and to transmit the impact signal to the adapter module 350. The impact signal can include a high voltage signal. When the acoustic transducer 102 receives the impact signal, an impact response signal is then generated from the acoustic transducer 102 in response to the impact signal. The acoustic transducer 102 also generates an acoustic signal in response to the impact signal. The acoustic signal can then be received by a target (e.g., the reflector 105 when in a testing environment), which then generates a reflected acoustic signal. The acoustic transducer 102 receives the reflected acoustic signal and generates a corresponding reflected signal.

The main module 310 can include a switch 316 (e.g., transmit/receive switch in FIG. 9) intermediate the pulser circuit 314 and the adapter module 350 to transmit the impact response signal and the reflected signal to the adapter module 350 from the pulser circuit 314 and to receive the impact response signal and the reflected signal from the signal processing component 354. The main module 310 can further include an amplifier 322 for amplifying the impact response signal and the reflected signal received from the signal processing component 354. The main module 310 can include a pre-amplifier 318 and a filter 320 intermediate the amplifier 322 and the switch 316.

Other configurations of the main module 310 are possible and some are described herein as example embodiments and are not intended to be limitations. For example, in some embodiments, the main module 310 can include the pulser circuit 314, the switch 316, and the amplifier 322. In some embodiments, the main module 310 can include the pulser circuit 314, the switch 316, the pre-amplifier 318, the filter 320, the amplifier 322, and an analog-to-digital converter (ADC) for converting analog signals to digital signals. In some embodiments, the main module 310 can include the pulser circuit 314, the switch 316, the filter 320, the amplifier 322, and the ADC. In some embodiments, the main module 310 can include the pulser circuit 314, the switch 316, the amplifier 322, and the ADC. In some embodiments, the main module 310 can include the pulser circuit 314, the switch 316, and the ADC. In some embodiments, the main module 310 can include the pulser circuit 314, the switch 316, the filter 320, and the ADC. In some embodiments, the main module 310 can include the pulser circuit 314, the switch 316, the pre-amplifier 318, the filter 320, and the ADC. In some embodiments, the main module 310 can include a digital-to-analog converter (DAC) for converting digital signals to analog signals, an amplifier intermediate the DAC and the switch 316 for amplifying the impact signal, and the amplifier 322. In some embodiments, the main module 310 can include the DAC, the amplifier intermediate the DAC and the switch 316, the pre-amplifier 318, the filter 320, the amplifier 322, and the ADC. In some embodiments, the main module 310 can include the DAC, the amplifier intermediate the DAC and the switch 316, the filter 320, the amplifier 322, and the ADC. In some embodiments, the main module 310 can include the DAC, the amplifier intermediate the DAC and the switch 316, the amplifier 322, and the ADC. In some embodiments, the main module 310 can include the DAC, the amplifier intermediate the DAC and the switch 316, and the ADC. In some embodiments, the main module 310 can include the DAC, the amplifier intermediate the DAC and the switch 316, the filter 320, and the ADC. In some embodiments, the main module 310 can include the DAC, the amplifier intermediate the DAC and the switch 316, the pre-amplifier 318, the filter 320, and the ADC. These example configurations of the main module 310 are intended only as examples and not as limitations.

The adapter controller 352 of the adapter module 350 is programmable to be compatible with a plurality of different acoustic transducers 102. The adapter controller 352 can operate to receive the test signal from the main module 310, and to then adapt the test signal based on operating parameters of the acoustic transducer 102 to be tested. The adapter controller 352 can be programmed to be compatible for communication with the acoustic transducer 102 prior to initiating testing of the acoustic transducer 102. In some embodiments, the microcontroller 312 can program the adapter controller 352 to configure the acoustic transducer 102 for testing. In some embodiments, the acoustic transducer 102 to be tested comprises an application-specific integrated circuit (ASIC) and the acoustic transducer 102 can be in communication with the adapter controller 352. For example, the microcontroller 312 can program the adapter controller 352 to configure an ASIC on an acoustic transducer 102 for testing. In some embodiments, the acoustic transducer 102 to be tested can be in direct communication with the microcontroller 312.

In some embodiments, the acoustic transducer 102 to be tested comprises analog switches that can be activated by the microcontroller 312. The adapter controller 352 then transmits the test signal to the acoustic transducer 102 via the transducer port 114. In some embodiments, a protective circuit is positioned intermediate the adapter controller 352 and the transducer port 114.

The adapter controller 352 may be any suitable processors, controllers or digital signal processors that can provide sufficient processing power depending on the configuration, purposes and requirements of the adapter module 350. In some embodiments, the adapter controller 352 can include more than one processor with each processor being configured to perform different dedicated tasks. For example, as shown in FIG. 9, the adapter controller 352 can include a field-programmable gate array (FPGA) programmable for adapting the test signal to the operating parameters of the acoustic transducer 102.

The signal processing component 354 can operate to receive one or more reflected signals from respective transducing elements 103 of the acoustic transducer 102 in response to the test signal and to convert the reflected signals to a transducer data signal that is representative of an operation state of the acoustic transducer 102.

As shown in FIG. 9, the signal processing component 354 can include one or more analog switches for converting the reflected signals to the transducer data signal. Due to the large number of transducing elements 103 at the acoustic transducer 102, there is a corresponding large number of reflected signals as each transducing element 103 generates a respective reflected signal. The signal processing component 354 can operate to reduce the large number of reflected signals into a reduced number of data lines, or the transducer data signal. In some embodiments, a single data line can be in communication with a plurality of transducing elements 103 of the acoustic transducer 102 via one or more analog switches of the signal processing component 354.

In some embodiments, the signal processing component 354 can include a multiplexer. For example, in some embodiments, the signal processing component 354 can comprise one or more analog switches that operate together with the microcontroller 312 to function as an analog multiplexer.

The signal processing component 354 can receive an operational signal from the main module 310. In some embodiments, the operational signal can configure the signal processing component 354 for testing. For example, the operational signal can activate a particular analog switch of the signal processing component 354 and deactivate other analog switches of the signal processing component 354 in order to test a particular transducing element 103 of the acoustic transducer 102.

Figures 7A, 7B:
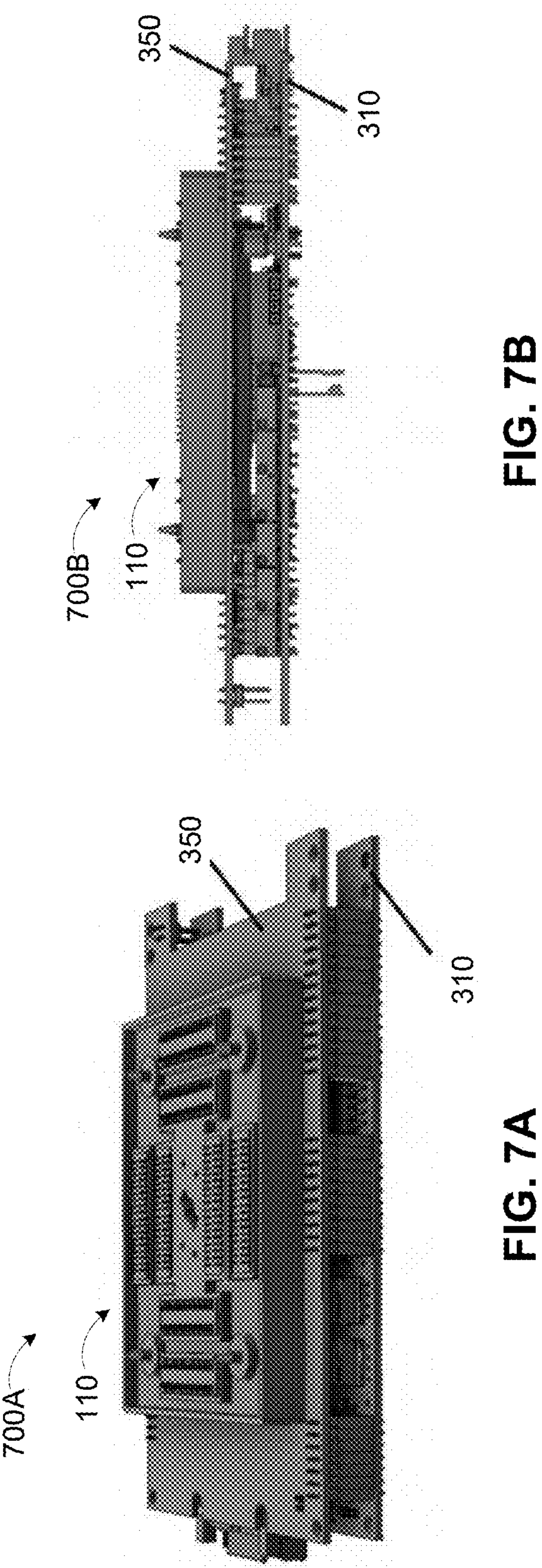
FIGS. 7A and 7B are different views of an example stacked configuration of the transducer adapter in accordance with an example embodiment.

In some embodiments, the main module 310 can be provided on a first printed circuit board and the adapter module 350 can be provided on a second printed circuit board electrically coupled to the first printed circuit board. The main module 310 can be stacked with the adapter module 350. FIGS. 7A and 7B are different views of an example stacked configuration of the transducer adapter 110. FIG. 7A shows a top perspective view of the main module 310 stacked to the adapter module 350, and FIG. 7B shows a side view of the stacked configuration of the transducer adapter 110.

Continuing with reference to FIG. 1, the acoustic transducer 102 being tested by the testing device 120 can include an ultrasound transducer. The acoustic transducer 102 being tested by the testing device 120 can have any number of transducing elements 103. For example, in some embodiments, the acoustic transducer 102 being tested by the testing device 120 can have one transducing element 103. As another example, in some embodiments, the acoustic transducer 102 being tested by the testing device 120 can have several thousand transducing elements 103.

The remote evaluation system 150 includes a remote controller 152, a remote storage component 154, and a remote interface component 156. As will be described with reference to FIG. 13, the remote evaluation system 150 can operate to determine an operation state of the acoustic transducer 102 being tested, while remote from the testing device 120.

The remote controller 152 can include any suitable processors, controllers or digital signal processors that can provide sufficient processing power depending on the configuration, purposes and requirements of the remote evaluation system 150. In some embodiments, the remote controller 152 can include more than one processor with each processor being configured to perform different dedicated tasks.

The remote storage component 154 can include RAM, ROM, one or more hard drives, one or more flash drives or some other suitable data storage elements such as disk drives, etc. may further include one or more databases (not shown) for storing information relating to, but not limited to, the acoustic transducers 102 and the transducer testing systems 130.

The remote interface component 156 may be any interface that enables the remote evaluation system 150 to communicate with other devices and systems. In some embodiments, the remote interface component 156 can include at least one of a serial port, a parallel port or a USB port. The remote interface component 156 may also include at least one of an Internet, Local Area Network (LAN), Ethernet, Firewire, modem or digital subscriber line connection. Various combinations of these elements may be incorporated within the remote interface component 156. For example, the remote interface component 156 may receive input from various input devices, such as a mouse, a keyboard, a touch screen, a thumbwheel, a track-pad, a track-ball, a card-reader, voice recognition software and the like depending on the requirements and implementation of the remote evaluation system 150.

It will be understood that in some embodiments, each of the remote controller 152, the remote storage component 154, and the remote interface component 156 may be combined into fewer number of modules or may be separated into further modules.

The network 140 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WIMAX), SS7 signaling network, fixed line, local area network, wide area network, and others, including any combination of these, capable of interfacing with, and enabling communication between, the transducer testing system 130 and the remote evaluation system 150.

The transducer testing system 130 can be operated to perform various tests for testing the operation state of the acoustic transducer 102. For example, the tests may include, but not limited to, a static test that includes an amplitude test and an impact response test, a dynamic test that includes an amplitude and depth analysis, an array cable diagnostic test, time of flight test, and an alignment test.

The static amplitude test can show echo intensity of individual transducing elements 103. The amplitude measured at the transducing element 103 is a measure of the echo intensity signal (peak-to-peak voltage, $V_{pp}$) of the individual transducing elements 103 within the acoustic transducer 102. Only minor variations in the signal amplitude of any given transducer element 103 within a fully functional array of transducing elements 103 are typically acceptable. Ideally, the echo intensity of each transducing element 103 should be identical. The resulting static amplitude bar graph should display a uniform intensity across the acoustic transducer 102. The static amplitude test can be applied to reveal various areas of issue or possible issue at the acoustic transducer 102, such as, the location and number of dead transducing elements 103, which could contribute to image drop-out, poor B-mode/2D image quality, reduced lateral resolution and noise in color mode; identification of transducing elements 103 that have reduced echo signal amplitude, which can contribute to poor B-mode/2D image quality and reduced lateral resolution; identification of lower doppler and color-flow sensitivity; and/or identification of noise in color mode.

The dynamic amplitude test measures the echo intensity of individual transducing elements 103. Element amplitude is a measure of the echo intensity signal (peak-to-peak voltage, $V_{pp}$) of the individual transducing elements 103. Only minor variations in the signal amplitude of any given transducing elements 103 within a fully functional array are typically acceptable. Ideally, the echo intensity of each transducing element 103 should be identical. The dynamic amplitude test can be used to reveal various areas of issue or possible issue at the acoustic transducer 102, such as, the location and number of dead transducing elements 103 which contribute to image drop-out, poor B-mode/2D image quality, reduced lateral resolution and noise in color mode; transducing elements 103 that have reduced echo signal amplitude, which can contribute to poor B-mode/2D image quality and reduced lateral resolution; lower doppler and color-flow sensitivity; noise in color mode; acoustic lens delamination; image drop-outs; and/or broken element wires within the transducer cable or connector port.

The time-of-flight test examines the time of flight (e.g., in microseconds) of echo signals and presents a bar graph based on the signals' travel time from the acoustic transducer 102 to the reflector 105 and back. The time-of-flight graph can display a uniform intensity across the transducing elements 103. Lower bars may indicate current dead/weak transducing elements 103. The time-of-flight can be used to reveal various areas of issue or possible issue at the acoustic transducer 102, such as, initial defects in the transducing elements 103; the location and number of currently dead transducing elements 103; image drop-outs; broken transducing elements wires within a transducer cable or connector port; and/or cable termination issues.

The array cable diagnostic may be used to reveal various areas of issue or possible issue at the acoustic transducer 102, such as, initial defects in the transducing elements 103 and transducing element wires at the early stages to prevent defects in the ultrasound beam former; the location and number of currently dead acoustic elements across the transducing elements 103; transducing elements 103 that have reduced impact response signal amplitude; noise in color mode; acoustic lens delamination; image drop-outs; broken transducing element wires within the transducer cable or connector port; and/or cable termination issues.

Figure 10:
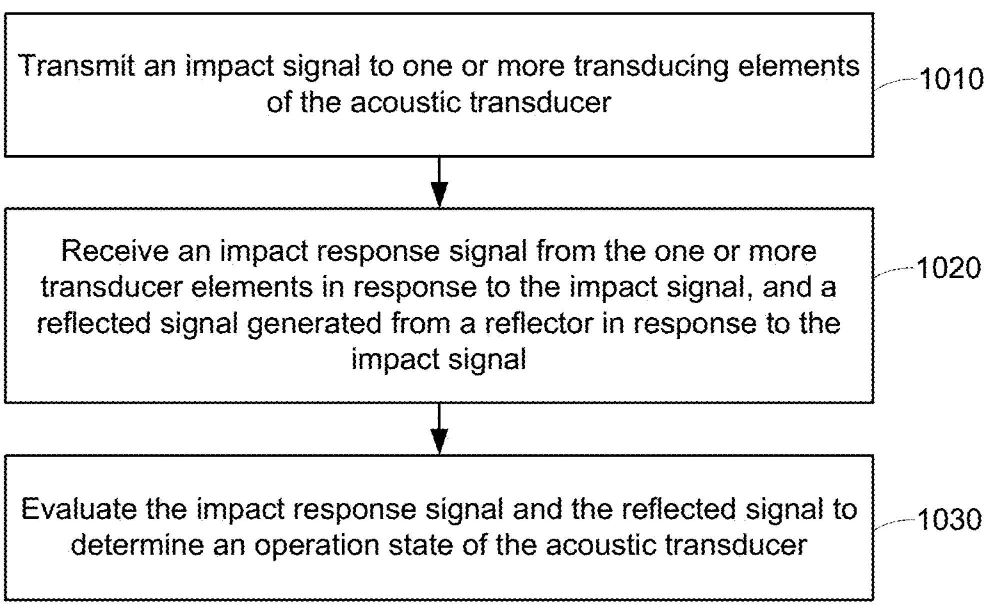
FIG. 10 is a flowchart showing an example method of testing an acoustic transducer.
Figures 11A, 11B, 11C:
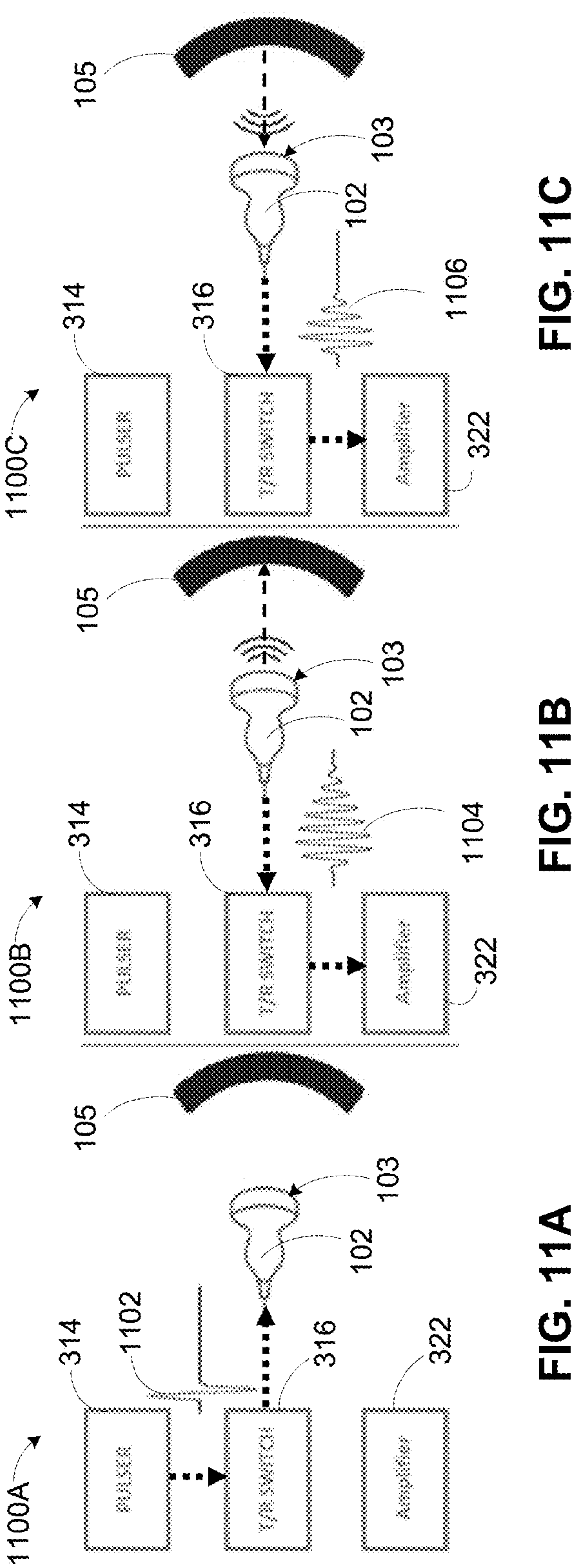
FIGS. 11A to 11C are block diagrams illustrating an example signal flow in accordance with the method of testing the acoustic transducer of FIG. 10.
Figure 12:
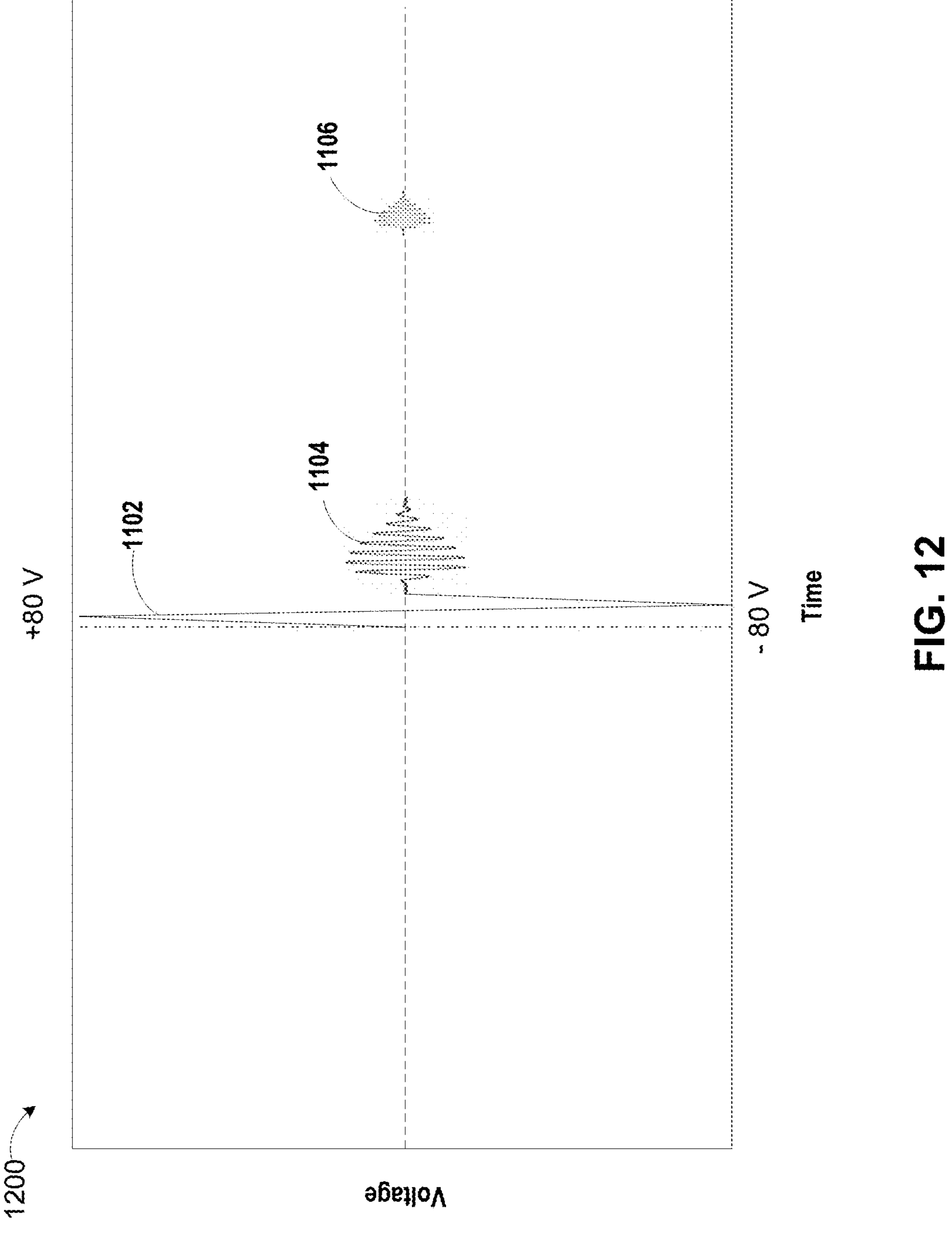
FIG. 12 is a graph showing an example signals during testing of the acoustic transducer in accordance with the method shown in FIG. 10.

An impact response test can also be applied by the testing device 120 to test the acoustic transducer 102. The impact response test can be conducted in a water bath. Reference will now be made to FIGS. 10, 11A to 11C and 12. FIG. 10 is a flowchart 1000 of the example method for testing the acoustic transducer 102 by applying the impact response test by the testing device 120. FIGS. 11A to 11C are block diagrams 1100A to 1100C, respectively, that illustrate an example signal flow for the method 1000. FIG. 12 is a graph showing an example signal flow when conducting the method 1000 with the transducer testing system 130.

The impact response test can be used to reveal various areas of issue or possible issues at the acoustic transducer 102, such as, initial defects in the transducing elements 103 and element wires at the early stages to prevent defects in the ultrasound beam former; location and number of current dead transducing elements 103; transducing elements 103 that have reduced impact response signal amplitude; noise in color mode; acoustic lens delamination; image drop-outs; broken transducing element wires within the transducer cable or connector port; and/or cable termination issues.

At 1010, transmitting an impact signal 1102 to one or more transducing elements 103 of the acoustic transducer 102 from the transducer testing system 130.

The impact signal 1102 can include a high voltage signal. The impact signal 1102 can include a pulse with a very small pulse width, but high peak-to-peak amplitude. For example, in FIG. 12, the impact signal 1102 can have a 12 nanoseconds pulse width, and peak-to-peak amplitude of 160V. At the moment of stimulation, the voltage may increase from 0V to +80V in 3 nanoseconds, and decreases to 0V in the next 3 nanoseconds, and then decreases to −80V in 3 nanoseconds, and finally return to 0V in 3 nanoseconds. As shown in FIGS. 11A to 11C, the impact signal 1102 can be generated from the pulser circuit 314 in some embodiments.

When the impact signal 1102 is applied to the transducing elements 103, the transducing elements 103 generate an impact response signal 1104 as well as an acoustic signal. When the acoustic signal collides with the reflector 105, the acoustic signal is reflected away from the reflector 105 towards the transducing elements 103. Due to the collision between the signal from the reflector 105 and the transducing element 103, the transducing elements 103 generate a reflected signal 1106.

The reflector 105 can include a metal plate in some embodiments.

At 1020, receiving, at the transducer testing system 130, an impact response signal 1104 from the one or more transducing elements 103 in response to the impact signal 1102 and a reflected signal 1106 generated from the reflector 105 in response to the impact signal 1102.

As shown in FIGS. 11A to 11C, the impact response signal 1104 and the reflected signal 1106 can be received at the testing device 120 via the switch 316 in some embodiments. The reflected signal 1106 will be received later than the impact response signal 1104, as shown in FIG. 12.

The impact response signal 1104, as shown in FIG. 12, can include information about the operation state of the transducing elements 103, and even a condition of the cable being used between the acoustic transducer 102 and the transducer adapter 110.

For example, the reflected signal 1106 can include information about whether a transducing element 103 is damaged or is dead. As another example, the impact response signal 1104 can include information about whether the cable being used between the acoustic transducer 102 and the transducer adapter 110 is damaged or otherwise faulty.

At 1030, evaluating, by the transducer testing system 130, the impact response signal 1104 and the reflected signal 1106 to determine an operation state of the acoustic transducer 102.

The transducer testing system 130 can evaluate the impact response signal 1104 to determine the operation state of each transducing element 103. In some embodiments, the impact response test can be used to examine the impact responses of the transducing elements 103 by presenting a bar graph generated based on impact response intensity amplitude. This result can be used to predict acoustic transducer health, including that of the transducing elements 103, transducer cable, and connector port. The impact response bar graph should ideally display a uniform intensity across the transducing elements. Very high or low bars can indicate current and likely future dead/weak transducing elements 103.

The transducer testing system 130 can evaluate the reflected signal 1106 to determine the operation state of each transducing element 103. In some embodiments, the peak-to-peak amplitude of the reflected signal 1106 can be evaluated to determine the operation state of each transducing element 103. For example, if the peak-to-peak amplitude for a given transducing element 103 is less than a predetermined threshold value, that transducing element 103 can be determined to be a weak element. In some embodiments, the predetermined threshold value can be a percentage of a maximum peak-to-peak amplitude. As another example, if the peak-to-peak amplitude for a given transducing element 103 is zero, that transducing element 103 can be determined to be dead.

The transducer testing system 130 can evaluate the impact response signal 1104 to determine the operation state of a transducer cable. In some embodiments, the transducer testing system 130 can presents a real-time bar graph based on the impact response intensity amplitude to predict acoustic transducer health, including that of the transducing elements 103, transducer cable and connector port. The bar graph should ideally display a uniform intensity across the transducing elements 103. Lower bars may indicate currently dead/weak elements, as well as initial defects in the transducing elements 103 and transducing elements wires at the very early stages. By evaluating the bar graphs based on the impact response signal 1104 and the reflected signal 1106, the transducer testing system 130 can determine whether a low signal is due to a dead or weak transducing element 103 or due to a damaged transducer cable.

The transducer testing system 130 can operate to predict a failure likelihood of the acoustic transducer 102 based on the impact response signal 1104, the reflected signal 1106 and the operation state of the acoustic transducer 102. For example, in some embodiments, if it is determined based on the response signal 1106 that an acoustic transducer 102 has one or more weak elements, the transducer testing system 130 can predict that the acoustic transducer 102 is likely to fail in the near future. As another example, in some embodiments, if it is determined based on the impact response signal 1104 that an acoustic transducer 102 has one or more damaged cables, the transducer testing system 130 can predict that the acoustic transducer 102 is likely to fail in the near future.

As briefly described with reference to FIG. 1, the remote evaluation system 150 can receive a test response signal from the transducer testing system 130 via the network 140. The remote evaluation system 150 can then evaluate the test response signal to determine the operation state of the acoustic transducer 102. Generally, acoustic transducers 102 are tested on site with the results reviewed by the operator of the transducer testing system 130. As the operator is often not a skilled technician of the transducer testing system 130 and/or the acoustic transducer 102, the results are often provided in such a way that does not require further detailed analysis. That is, the operator of the transducer testing system 130 is likely unable to properly interpret detailed test data that can offer more information on the operation state of the acoustic transducer 102—e.g., whether the acoustic transducer 102 likely requires maintenance soon to minimize more extensive damage, and/or whether the acoustic transducer 102, despite being near scheduled maintenance date, is operating at a level that does not justify the need for the maintenance, etc.

The methods and systems disclosed herein enable remote evaluation of the operation state of the acoustic transducer 102, as will be described with reference to FIG. 13. Further, with the remote evaluation system 150, more computing resources can be available (in comparison with the transducer testing system 130) in some embodiments to offer more extensive evaluation of the test response signal received from the transducer testing system 130.

Figure 13:
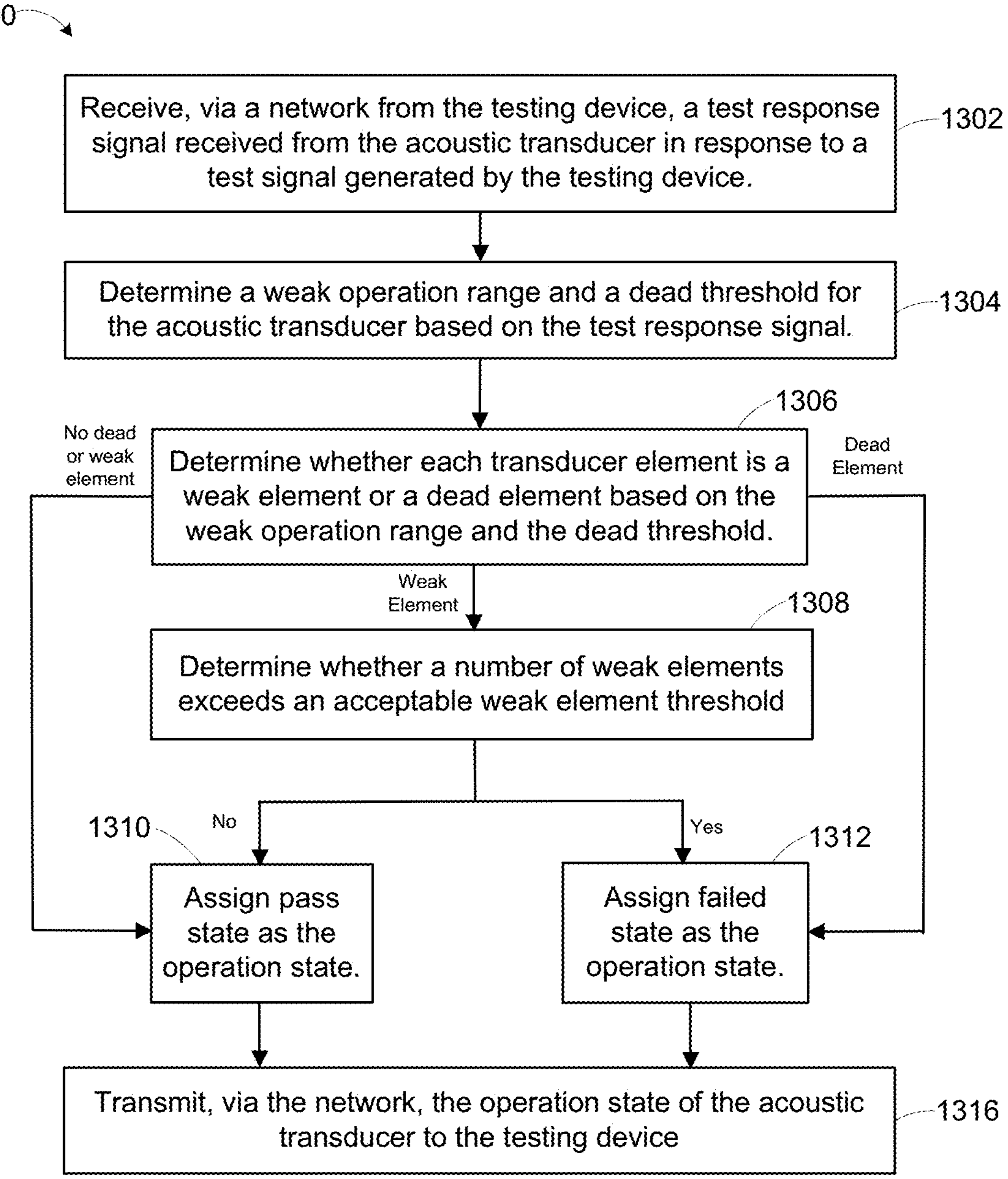
FIG. 13 is a flowchart showing an example method of operating a remote evaluation system to determine an operation state of an acoustic transducer The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

FIG. 13 is a flowchart 1300 of an example method of operating the remote evaluation system 150 to determine the operation state of the acoustic transducer 102.

At 1302, the remote controller 152 receives, via the network 140 from the testing device 120, a test response signal received from the acoustic transducer 102 in response to a test signal generated by the testing device 120.

The test response signal can include transducer device data in respect of the acoustic transducer 102. The remote controller 152 can determine from the transducer device data various characteristics of the acoustic transducer 102, such as but not limited to, a number of transducing elements 103. In some embodiments, the remote controller 152 can determine from the transducer device data an identifier identifying a model and/or type of the acoustic transducer 102, and the remote controller 152 can then determine the characteristics of the acoustic transducer 102 from the data stored in the remote storage component 154.

The test response signal can include a response signal from each transducing element 103 of the plurality of transducing elements 103 of the acoustic transducer 102. The response signal can include a voltage peak-to-peak signal.

At 1304, determine a weak operation range and a dead threshold for the acoustic transducer 102 based on the test response signal.

The weak operation range and the dead threshold can vary with acoustic transducers 102. In some embodiments, the remote controller 152 can determine the weak operation range and/or the dead threshold based at least on device characteristics determined from the transducer device data.

For each acoustic transducer 102, the remote controller 152 can determine the weak operation range and the dead threshold for the acoustic transducer 102 based on the test response signal and the number of transducing elements 103 at the acoustic transducer 102. For example, the remote controller 152 can determine an average amplitude for the test response signal and can then define the weak operation range based on the average amplitude. The remote controller 152 can define the weak operation range by setting a lower end of the weak operation range and an upper end of the weak operation range with respect to the average amplitude. For example, the weak operation range can be defected based on a lower factor of the average amplitude and a higher factor of the average amplitude, such as 0.4 of the average amplitude and 0.75 of the average amplitude. Other factors of the average amplitude may apply depending on various factors, such as but not limited to, the type of acoustic transducer 102 and/or the intended usage of the acoustic transducer 102.

In respect of the dead threshold, the remote controller 152 can determine a maximum amplitude within the test response signal and assign the dead threshold with respect to the maximum amplitude. For example, the dead threshold can correspond to a factor of the maximum amplitude, such as 0.1 of the maximum amplitude. Other factors of the maximum amplitude may apply depending on various factors, such as but not limited to, the type of acoustic transducer 102 and/or the intended usage of the acoustic transducer 102.

At 1306, for each transducing element 103 of the plurality of transducing elements 103, determine whether that transducing element 103 is one of a weak element and a dead element based on the weak operation range and the dead threshold.

The remote controller 152 can determine that the transducing element 103 is neither weak nor dead when the response signal associated with that transducing element 103 is above the weak operation range. That transducing element 103 can then be identified as a good element. When all transducing elements 103 are determined to be good elements, the remote controller 152 can assign the pass state as the operation state for the acoustic transducer 102 (at 1310).

The remote controller 152 determines the transducing element 103 is a weak element when the response signal associated with that transducing element 103 is within the weak operation range. In some embodiments, the remote controller 152 can determine the transducing element 103 is associated with an unknown state when the associated response signal is between the weak operation range and the dead threshold.

The remote controller 152 determines the transducing element 103 is a dead element when the response signal associated with that transducing element 103 is below the dead threshold. The remote controller 152 assigns a failed state as the operation state of the acoustic transducer 102 in response to determining the transducing element 103 is the dead element (at 1312).

At 1308, when there is no dead element, the remote controller 152 determines whether a number of weak elements exceeds an acceptable weak element threshold.

The acceptable weak element threshold corresponds to a number of weak transducing elements 103, and/or a number of consecutive weak transducing elements 103 at the acoustic transducer 102 that could still offer an acceptable operation level for the intended use. The acceptable weak element threshold can vary depending on various factors, such as but not limited to, the type of acoustic transducer 102 and/or the intended usage of the acoustic transducer 102. The remote controller 152 can assign the failed state as the operation state of the acoustic transducer 102 when the number of weak elements exceeds the acceptable weak element threshold (at 1312).

In some embodiments, the remote controller 152 can determine whether a number of weak elements exceeds a maximum number of weak elements. When the remote controller 152 determines that the number of weak elements exceeds the maximum number of weak elements, the remote controller 152 assigns the failed state as the operation state of the acoustic transducer 102 (at 1312). The maximum number of weak elements can correspond to a number of weak transducing elements 103 at the acoustic transducer 102 that could still offer an acceptable operation level for the intended use. Example maximum number of weak elements can be four, but this value can vary.

The remote controller 152 can, in some embodiments, determine whether the number of weak elements includes two or more consecutive weak elements, and assign the failed state as the operation state of the acoustic transducer 102 in response to determining the number of weak elements includes two or more consecutive weak elements (at 1312). Consecutive weak elements can be particularly problematic for certain acoustic transducers 102 as more data at adjacent sections of the target would be excluded, or at least reduced in quality. For applications where the target is narrower and/or the data being collected is highly critical for diagnostic purposes, consecutive weak elements can adversely affect the operation level of the acoustic transducer 102.

At 1310, the remote controller 152 assigns a pass state as the operation state of the acoustic transducer 102.

The remote controller 152 can indicate that the acoustic transducer 102 is in the pass state such that it continues to be operational for the intended application despite some defects at the transducing elements 103.

At 1316, the remote controller 152 transmits, via the network 140, the operation state of the acoustic transducer 102 to the testing device 120.

It will be appreciated that numerous specific details are set forth in order to provide a thorough understanding of the example embodiments described herein. However, it will be understood by those of ordinary skill in the art that the embodiments described herein may be practiced without these specific details. Furthermore, this description and the drawings are not to be considered as limiting the scope of the embodiments described herein in any way, but rather as describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies. It should be noted that the term "coupled" used herein indicates that two elements can be directly coupled to one another or coupled to one another through one or more intermediate elements.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high-level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims.

We claim:

1. An acoustic transducer adapter for coupling an acoustic transducer to a testing device, the acoustic transducer adapter comprising:

a main module in communication with the testing device, the main module operable to receive a test signal from the testing device; and an adapter module electrically coupled to the main module, the adapter module comprising:

an adapter controller programmable to be compatible with a plurality of different acoustic transducers, the adapter controller operable to:

receive the test signal from the main module;

adapt the test signal based on one or more operating parameters of the acoustic transducer; and transmit the test signal to the acoustic transducer; and a signal processing component for receiving one or more reflected signals from one or more respective transducing elements of the acoustic transducer in response to the test signal and converting the one or more reflected signals to a transducer data signal representative of an operation state of the acoustic transducer.

2. The acoustic transducer adapter of claim 1, wherein the main module and the adapter module are stacked.

3. The acoustic transducer adapter of claim 1, wherein the main module is provided on a first printed circuit board and the adapter module is provided on a second printed circuit board electrically coupled to the first printed circuit board.

4. The acoustic transducer adapter of claim 1, wherein the signal processing component comprises one or more analog switches.

5. The acoustic transducer adapter of claim 1, wherein the signal processing component comprises a multiplexer.

6. The acoustic transducer adapter of claim 1, wherein the adapter module comprises an adapter module connection port for coupling the adapter module to the acoustic transducer, and a protective circuit intermediate the adapter controller and the adapter module connection port.

7. The acoustic transducer adapter of claim 1, wherein the signal processing component is operable to receive an operational signal from the main module.

8. The acoustic transducer adapter of claim 1, wherein the adapter controller is programed to be compatible for communication with the acoustic transducer prior to initiating testing of the acoustic transducer.

9. The acoustic transducer adapter of claim 1, wherein the plurality of different acoustic transducers comprising one or more acoustic transducers manufactured by different manufacturers.

10. The acoustic transducer adapter of claim 1, wherein the acoustic transducer comprises an ultrasound transducer.

11. The acoustic transducer adapter of claim 1, wherein the main module comprises:

a main controller for receiving the test signal from the testing device; and a pulser circuit for generating an impact signal based on the test signal and transmitting the impact signal to the adapter module, resulting in an impact response signal being generated from the acoustic transducer in response to a high voltage signal.

12. The acoustic transducer adapter of claim 11, wherein the main module further comprises a switch intermediate the pulser circuit and the adapter module, the switch operating to transmit the impact signal to the adapter module from the pulser circuit and to receive the impact response signal from the signal processing component.

13. The acoustic transducer adapter of claim 12, wherein the main module further comprises an amplifier for amplifying the impact response signal received from the acoustic transducer.

14. The acoustic transducer adapter of claim 11, wherein the impact signal comprises a signal having a high voltage value.

15. The acoustic transducer adapter of claim 11, wherein the main module further comprises a first main module connection port for coupling the main module to the testing device to communicate via one or more analog switch or multiplexer, and a second connection port for coupling the adapter module to the acoustic transducer.

16. The acoustic transducer adapter of claim 11, wherein the main module further comprises a switch intermediate the pulser circuit and the signal processing component, the switch operating to transmit the impact signal to the acoustic transducer via the signal processing component and to receive the impact response signal from the acoustic transducer via the signal processing component.

17. The acoustic transducer adapter of claim 16, wherein the main module further comprises an amplifier to amplify the impact response signal received from the acoustic transducer via the signal processing component, and one or more filters to remove noise from the received impact response signal.

18. An acoustic transducer testing system comprising:

a device controller operable to generate a test signal; and one or more connection ports for coupling to one or more acoustic transducer adapters defined in claim 1 for receiving the test signal to test one or more different acoustic transducers.

19. The acoustic transducer testing system of claim 18, wherein the main module and the adapter module are stacked.

20. The acoustic transducer testing system of claim 18, wherein the main module is provided on a first printed circuit board and the adapter module is provided on a second printed circuit board electrically coupled to the first printed circuit board.

21. The acoustic transducer testing system of claim 18, wherein the main module comprises:

a main controller for receiving the test signal from the testing device; and a pulser circuit for generating an impact signal based on the test signal and transmitting the impact signal to the adapter module, resulting in an impact response signal being generated from the acoustic transducer in response to a high voltage signal.

22. The acoustic transducer testing system of claim 18, wherein the main module further comprises a switch intermediate the pulser circuit and the adapter module, the switch operating to transmit the impact signal to the adapter module from the pulser circuit and to receive the impact response signal from the signal processing component.

23. The acoustic transducer testing system of claim 18, wherein the main module further comprises a switch intermediate the pulser circuit and the signal processing component, the switch operating to transmit the impact signal to the acoustic transducer via the signal processing component and to receive the impact response signal from the acoustic transducer via the signal processing component.

* * * * *